(12) United States Patent
Oda

(10) Patent No.: US 11,372,010 B2
(45) Date of Patent: Jun. 28, 2022

(54) ANALYSIS APPARATUS, ANALYSIS SYSTEM, METHOD FOR MANAGING ANALYSIS APPARATUS, AND PROGRAM

(71) Applicant: FUJIFILM Corporation, Tokyo (JP)

(72) Inventor: Yoshinari Oda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 135 days.

(21) Appl. No.: 16/524,158

(22) Filed: Jul. 28, 2019

(65) Prior Publication Data
US 2019/0346467 A1 Nov. 14, 2019

Related U.S. Application Data

(63) Continuation of application No. PCT/JP2018/001684, filed on Jan. 19, 2018.

(30) Foreign Application Priority Data

Jan. 30, 2017 (JP) .............................. JP2017-014590

(51) Int. Cl.
*G01N 35/00* (2006.01)

(52) U.S. Cl.
CPC ... *G01N 35/00871* (2013.01); *G01N 35/0092* (2013.01); *G01N 2035/0091* (2013.01); *G01N 2035/0097* (2013.01)

(58) Field of Classification Search
CPC ............. G05B 19/418; G01N 35/0092; G01N 2035/0091; G01N 33/48; G01N 35/00871; G01N 2035/0097; G16H 40/20
See application file for complete search history.

(56) References Cited

U.S. PATENT DOCUMENTS

2003/0229475 A1  12/2003  Osaka et al.
2007/0196909 A1*  8/2007  Showalter .............. G06Q 10/00
                                              435/283.1
(Continued)

FOREIGN PATENT DOCUMENTS

CN          1467972        1/2004
CN         101403894       4/2009
(Continued)

OTHER PUBLICATIONS

"Office Action of Japan Counterpart Application", dated Feb. 25, 2020, with English translation thereof, p. 1-p. 5.
(Continued)

*Primary Examiner* — Shogo Sasaki
(74) *Attorney, Agent, or Firm* — JCIPRNET

(57) ABSTRACT

An analysis system 1 includes analysis apparatuses 2A to 2E which are dispersively installed in a plurality of installation places and are connected through a network 3 so as to be communicable with each other. At least one analysis apparatus in each installation place includes: an information collection unit 20 that collects analysis progress information of the host analysis apparatus and the other analysis apparatuses and required movement time information of each of the other analysis apparatuses indicating the required movement time which is the time required for an operator to move from the installation place of the host analysis apparatus to the installation places of the other analysis apparatuses; a search unit 21 that searches for an analysis apparatus that is available first among the host analysis apparatus and the other analysis apparatuses on the basis of the collected analysis progress information and the collected required movement time information; and a display control unit 22 that displays information indicating the searched analysis (Continued)

| ANALYSIS APPARATUS | STATE | WAITING TIME | REQUIRED MOVEMENT TIME |
|---|---|---|---|
| A | IN ANALYSIS OPERATION | 15 MINUTES | - |
| B | IN ANALYSIS OPERATION | 5 MINUTES | 0 |
| C | IN ANALYSIS OPERATION | 15 MINUTES | 0 |
| D | IN STANDBY STATE | 0 | 10 MINUTES |
| E | IN ANALYSIS OPERATION | 10 MINUTES | 10 MINUTES | apparatus that is available first on a display unit 12 of the analysis apparatus.

13 Claims, 4 Drawing Sheets

(56) References Cited

U.S. PATENT DOCUMENTS

| | | | | |
|---|---|---|---|---|
| 2008/0235055 | A1* | 9/2008 | Mattingly | G06Q 10/10 705/3 |
| 2009/0118856 | A1 | 5/2009 | Nakagawa et al. | |
| 2009/0130765 | A1* | 5/2009 | Bauer | G16H 10/40 436/43 |
| 2010/0004776 | A1 | 1/2010 | Maida | |
| 2010/0223556 | A1 | 9/2010 | Wakabayashi et al. | |
| 2012/0109531 | A1* | 5/2012 | Knafel | G05B 19/41865 702/19 |
| 2018/0052140 | A1 | 2/2018 | Yokoi | |
| 2018/0340949 | A1* | 11/2018 | Maetzler | G01N 35/00732 |

FOREIGN PATENT DOCUMENTS

| | | |
|---|---|---|
| CN | 101652727 | 2/2010 |
| JP | H05134989 | 6/1993 |
| JP | 2004085356 | 3/2004 |
| JP | 2008250457 | 10/2008 |
| JP | 2008292328 | 12/2008 |
| JP | 2009250657 | 10/2009 |
| JP | 2013218643 | 10/2013 |
| JP | 2014174901 | 9/2014 |
| JP | 2016113237 | 6/2016 |
| WO | 2008117419 | 10/2008 |
| WO | 2016157516 | 10/2016 |

OTHER PUBLICATIONS

"Search Report of Europe Counterpart Application", dated Nov. 13, 2019, p. 1-p. 9.

"International Search Report (Form PCT/ISA/210) of PCT/JP2018/001684," dated Mar. 13, 2018, with English translation thereof, pp. 1-5.

"Written Opinion of the International Searching Authority (Form PCT/ISA/237) of PCT/JP2018/001684," dated Mar. 13, 2018, with English translation thereof, pp. 1-8.

"Office Action of China Counterpart Application," with English translation thereof, dated Feb. 3, 2020, p. 1-p. 20.

"Office Action of China Counterpart Application", dated May 6, 2020, with English translation thereof, pp. 1-18.

* cited by examiner

FIG. 3

| ANALYSIS APPARATUS | STATE | WAITING TIME (min) | REQUIRED MOVEMENT TIME (min) | AVAILABLE REQUIRED TIME (min) |
|---|---|---|---|---|
| A | IN ANALYSIS OPERATION | 15 | - | - |
| B | IN ANALYSIS OPERATION | 5 | 0 | 5 |
| C | IN ANALYSIS OPERATION | 15 | 0 | 15 |
| D | IN STANDBY STATE | 0 | 10 | 10 |
| E | IN ANALYSIS OPERATION | 10 | 10 | 10 |

FIG. 4

| ANALYSIS APPARATUS | STATE | WAITING TIME (min) | REQUIRED MOVEMENT TIME (min) | AVAILABLE REQUIRED TIME (min) |
|---|---|---|---|---|
| A | IN ANALYSIS OPERATION | 15 | 10 | 15 |
| B | IN ANALYSIS OPERATION | 5 | 10 | 10 |
| C | IN ANALYSIS OPERATION | 15 | 10 | 15 |
| D | IN STANDBY STATE | 0 | - | - |
| E | IN ANALYSIS OPERATION | 10 | 0 | 10 |

FIG. 5

| ANALYSIS APPARATUS | STATE | WAITING TIME | REQUIRED MOVEMENT TIME |
|---|---|---|---|
| A | IN ANALYSIS OPERATION | 15 MINUTES | - |
| B | IN ANALYSIS OPERATION | 5 MINUTES | 0 |
| C | IN ANALYSIS OPERATION | 15 MINUTES | 0 |
| D | IN STANDBY STATE | 0 | 10 MINUTES |
| E | IN ANALYSIS OPERATION | 10 MINUTES | 10 MINUTES |

FIG. 6

| ANALYSIS APPARATUS | STATE |
|---|---|
| B | IN ANALYSIS OPERATION (5 MINUTES REMAINING) |

ANALYSIS APPARATUS, ANALYSIS SYSTEM, METHOD FOR MANAGING ANALYSIS APPARATUS, AND PROGRAM

CROSS REFERENCE TO RELATED APPLICATION

This is a continuation of International Application No. PCT/JP2018/001684 filed on Jan. 19, 2018, and claims priority from Japanese Patent Application No. 2017-014590 filed on Jan. 30, 2017, the entire disclosures of which are incorporated herein by reference.

BACKGROUND OF THE INVENTION

1. Field of the Invention

The present invention relates to an analysis apparatus, an analysis system, a method for managing an analysis apparatus, and a computer readable medium storing a program.

2. Description of the Related Art

An analysis apparatus that detects or quantifies a virus in a sample using an antigen-antibody reaction has been used to examine a viral infection such as influenza. This type of analysis apparatus can analyze samples relatively quickly and easily. In some cases, a plurality of analysis apparatuses are used to analyze a large number of samples.

In an analysis system disclosed in JP2004-085356A, a plurality of analysis apparatuses are connected to each other by a network and the scheduled analysis end time of each analysis apparatus is collected through the network. Then, a list of the collected scheduled analysis end times of the analysis apparatuses is displayed on a display screen of a personal computer connected to the same network or the display screens of the analysis apparatuses.

Since the list of the collected scheduled analysis end times of the analysis apparatuses is displayed, it is easy to search for an available analysis apparatus and the operation efficiency of a plurality of analysis apparatuses is improved.

SUMMARY OF THE INVENTION

The analysis system disclosed in JP2004-085356A is configured such that the operator searches for the analysis apparatus that is available first on the basis of the scheduled analysis end time of each analysis apparatus. However, in a case in which a plurality of analysis apparatuses are dispersively installed in a plurality of installation places, an analysis apparatus with the earliest scheduled analysis end time is not necessarily the analysis apparatus that is available first.

For example, in a case in which an installation place A of the analysis apparatus with the earliest scheduled analysis end time is different from an installation place B of a personal computer or an analysis apparatus which has presented the scheduled analysis end time of each analysis apparatus to the operator and the analysis apparatus installed in the installation place B is available while the operator is moving from the installation place B to the installation place A, the analysis apparatus installed in the installation place B is the analysis apparatus that is available first.

As such, the analysis apparatus that is available first is not appropriately searched by only the scheduled analysis end time of each analysis apparatus, which makes it difficult to improve the operation efficiency of a plurality of analysis apparatuses. Even in a case in which the time required for the operator to move between a plurality of installation places is considered by the operator, a burden on the operator increases as the number of analysis apparatuses and the number of installation places increase. As a result, the usability of the system is reduced.

The invention has been made in view of the above-mentioned problems and an object of the invention is to improve the operation efficiency and usability of a plurality of analysis apparatuses.

According to an aspect of the invention, there is provided an analysis apparatus that is connected to other analysis apparatuses so as to be communicable with each other. The analysis apparatus, being a host analysis apparatus, comprises: an information collection unit that collects analysis progress information of the host analysis apparatus and the other analysis apparatuses and required movement time information of each of the other analysis apparatuses indicating a required movement time which is a time required for an operator to move from an installation place of the host analysis apparatus to installation places of the other analysis apparatuses; a search unit that searches for an analysis apparatus that is available first among the host analysis apparatus and the other analysis apparatuses on the basis of the analysis progress information and the required movement time information collected by the information collection unit; and a display control unit that displays information indicating the analysis apparatus that is available first searched by the search unit on a display unit of the analysis apparatus.

According to another aspect of the invention, there is provided an analysis system comprising a plurality of analysis apparatuses that are dispersively installed in a plurality of installation places and are connected so as to be communicable with each other. At least one analysis apparatus in each installation place is the analysis apparatus.

According to still another aspect of the invention, there is provided a method for managing a plurality of analysis apparatuses that are connected so as to be communicable with each other. At least one of the plurality of analysis apparatuses is a host analysis apparatus, The management method comprises: an information collection step, executed by a processor of the host apparatus, to collect analysis progress information of the host analysis apparatus and the other analysis apparatuses and required movement time information of each of the other analysis apparatuses indicating a required movement time which is a time required for an operator to move from an installation place of the host analysis apparatus to installation places of the other analysis apparatuses; a search step of allowing the processor to search for an analysis apparatus that is available first among the host analysis apparatus and the other analysis apparatuses on the basis of the analysis progress information and the required movement time information collected in the information collection step; and a display step of allowing the processor to display information indicating the analysis apparatus that is available first searched in the search step on a display unit of the analysis apparatus.

According to yet another aspect of the invention, there is a non-transitory computer readable medium storing a program that causes a processor to perform each step of the management method.

According to the invention, it is possible to improve the operation efficiency and usability of a plurality of analysis apparatuses.

BRIEF DESCRIPTION OF THE DRAWINGS

FIG. 3 is a table illustrating an example of the search results of an analysis apparatus that is available first.

FIG. 4 is a table illustrating an example of the search results of the analysis apparatus that is available first.

FIG. 5 is a diagram schematically illustrating an example of the display of information indicating the analysis apparatus that is available first.

FIG. 6 is a diagram schematically illustrating another example of the display of the information indicating the analysis apparatus that is available first.

DESCRIPTION OF THE PREFERRED EMBODIMENTS

Figure 1:
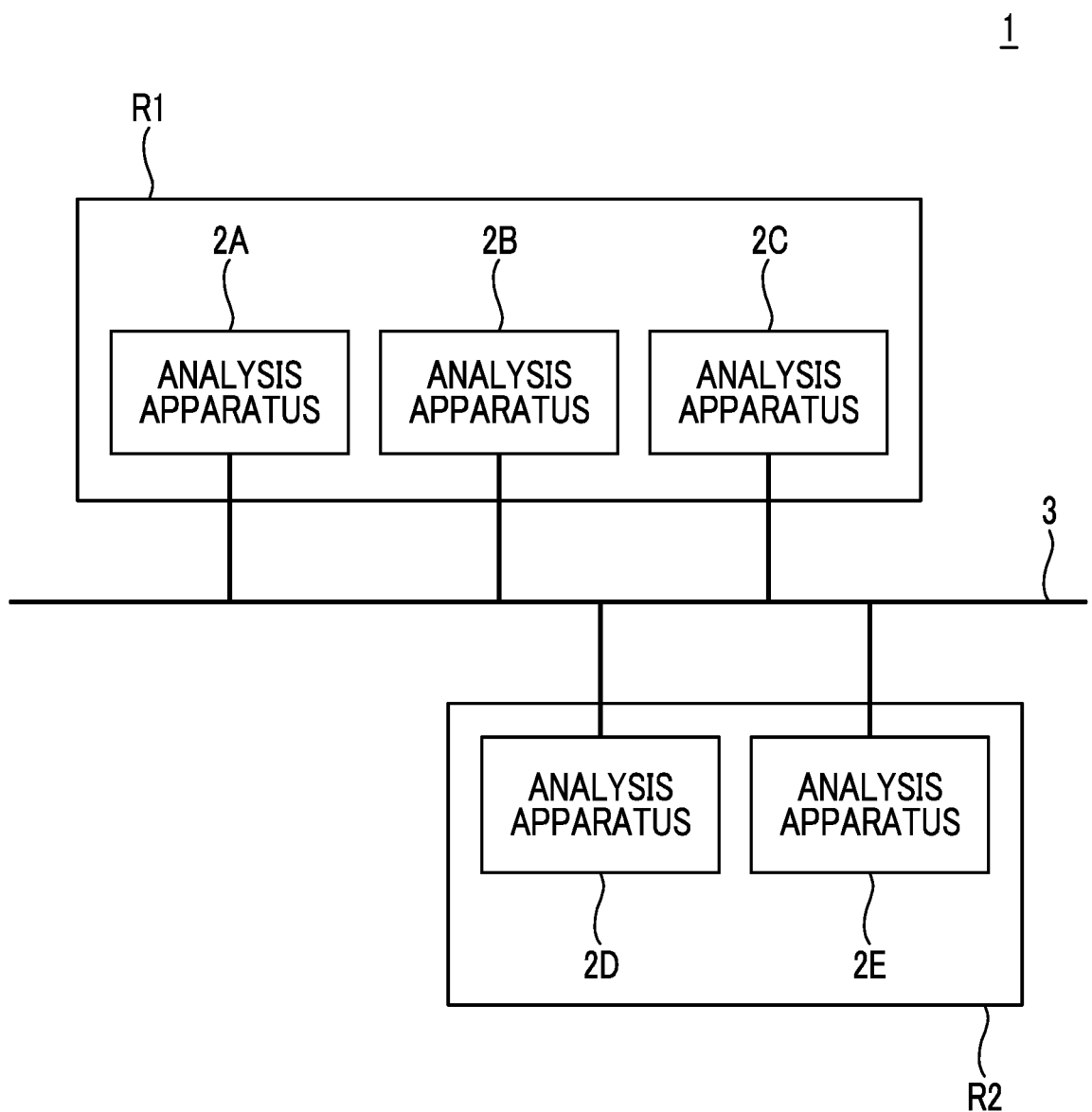
FIG. 1 is a diagram schematically illustrating an example of an analysis system for describing an embodiment of the invention.

FIG. 1 illustrates an example of an analysis system for describing an embodiment of the invention.

An analysis system 1 comprises a plurality of analysis apparatuses 2A to 2E that can perform the same type of analysis. An immunochromatographic apparatus can be given as an example of the analysis apparatus.

The immunochromatographic apparatus detects or quantifies an antigen (analyte), such as a virus, in a sample liquid using an antigen-antibody reaction. Specifically, a sample liquid is dropped onto a chromatography test piece which is, for example, a cellulose membrane. The dropped sample liquid flows through the test piece by capillary action. A labeled antibody which is labeled with gold colloid particles is provided in a portion of the test piece onto which the sample liquid is dropped. In a case in which the sample liquid contains an antigen, the antigen and the labeled antibody are bound to form an antigen-antibody complex. The antigen-antibody complex is moved by the flow of the sample liquid.

Then, a reactive portion is provided on the downstream side of the test piece through which the sample liquid flows. A capture antibody bound to the antigen is fixedly provided in the reactive portion. The antigen-antibody complex moved by the flow of the sample liquid is captured by the capture antibody in the reactive portion and is fixed to the reactive portion. Since the antigen-antibody complex is fixed to the reactive portion, the reactive portion is colored by the gold colloid particles attached to the labeled antibody of the antigen-antibody complex. As the amount of fixed antigen-antibody complex becomes larger, the color of the reactive portion becomes stronger. The color of the reactive portion is optically detected as a change in absorbance and the antigen in the sample liquid is detected or quantified.

In addition, the analysis apparatuses that can perform the same type of analysis are analysis apparatuses that can detect or quantify the same analyte, using the same analysis method. The analysis apparatuses do not need to be the same type. In addition, the analysis apparatuses 2A to 2E are not limited to the immunochromatographic apparatuses and may be other analysis apparatuses.

The analysis apparatuses 2A to 2E are dispersively installed in a plurality of installation places and are connected through a network 3, such as a local area network (LAN), so as to communicable with each other. It is assumed that the analysis apparatuses 2A to 2E are immunochromatographic apparatuses. The immunochromatographic apparatuses are used in medical facilities such as hospitals. In this example, the analysis apparatuses 2A to 2E are dispersively installed in different rooms of one medical facility. The analysis apparatuses 2A to 2C are installed in a room R1 (for example, a clinical laboratory) and the other analysis apparatuses 2D and 2E are installed in a room R2 (for example, an emergency room).

In addition, the plurality of installation places may be different rooms in the same facility as in this example or may be different facilities.

Figure 2:
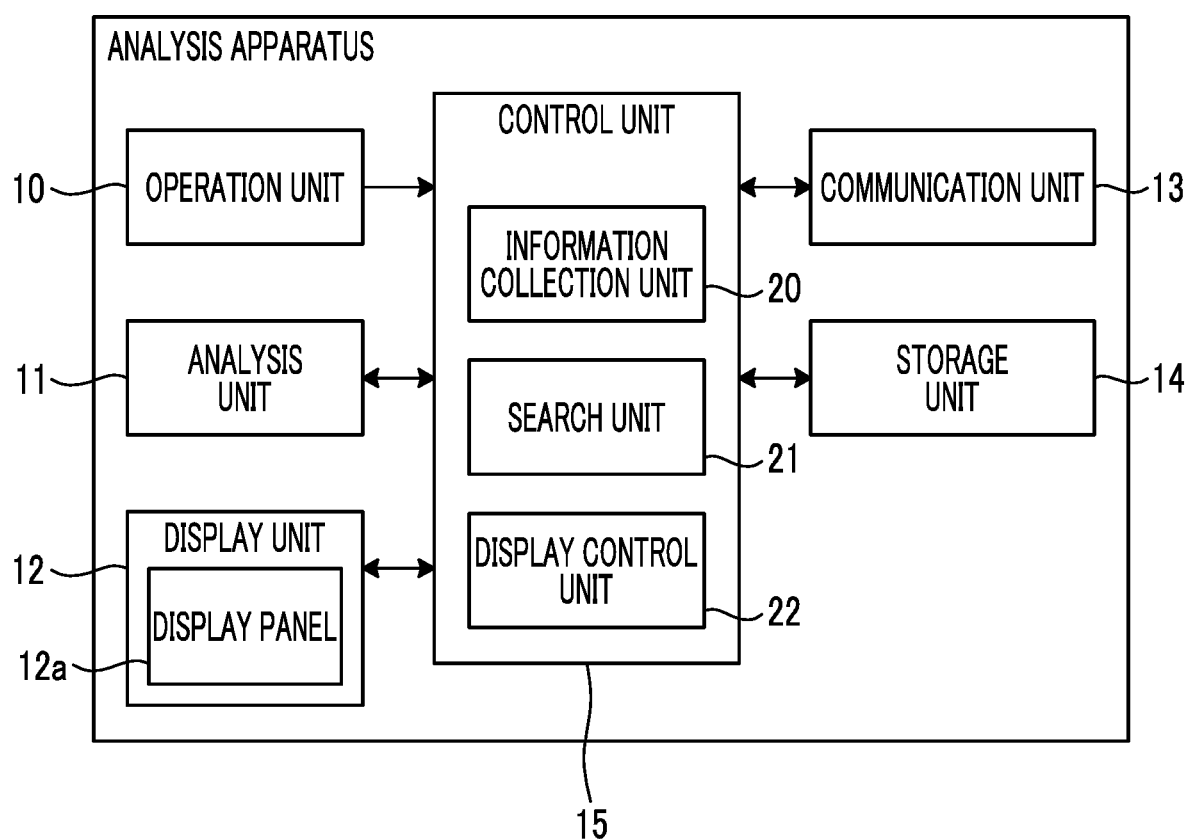
FIG. 2 is a block diagram illustrating an example of an analysis apparatus forming the analysis system illustrated in FIG. 1.

FIG. 2 illustrates an example of the configuration of the analysis apparatus 2A. In addition, the other analysis apparatuses 2B to 2E have the same configuration as the analysis apparatus 2A which will be described below.

The analysis apparatus 2A comprises an operation unit 10, an analysis unit 11, a display unit 12, a communication unit 13, a storage unit 14, and a control unit 15 that controls the overall operation of the operation unit 10, the analysis unit 11, the display unit 12, the communication unit 13, and the storage unit 14.

The operation unit 10 receives various commands (for example, an analysis start command) from an operator. The operation unit 10 includes, for example, hardware keys such as switches. The commands received by the operation unit 10 are input to the control unit 15.

The analysis unit 11 is appropriately configured according to analysis performed by the analysis apparatus. The immunochromatographic apparatus includes, for example, an imaging unit that captures an image of a chromatography test piece using an imaging element, such as a charge-coupled device (CCD) or a complementary metal oxide semiconductor (CMOS), and an image analysis unit that analyzes the image of the test piece acquired by the imaging unit. The color of a reactive portion in the image of the test piece is digitized by the image analysis unit and an analyte in a sample liquid is detected or quantified. The analysis result is input to the control unit 15.

The display unit 12 presents various kinds of information (for example, the analysis result) to the operator. The display unit 12 includes a display panel 12a, such as a liquid crystal display (LCD) or an organic electro-luminescence display (OELD), and displays images or characters on a display screen of the display panel 12a to present information. In addition, the display unit 12 may further include a display lamp, such as a light emitting diode (LED), and provide information using the lighting state (turn-on, blinking, or turn-off) of the display lamp. In addition, the display panel 12a may be a so-called touch panel that detects an operation on a display screen. In this case, the display panel 12a partially or entirely functions as the operation unit 10 that receives various commands from the operator.

The communication unit 13 is connected to the network 3 and transmits and receives information through the network 3. The communication unit 13 is a hardware interface corresponding to the network to which the communication unit 13 is connected.

The storage unit 14 stores a control program and control data executed by the control unit 15 and various kinds of information such as the analysis results. The storage unit 14 is a storage medium such as a flash memory, a hard disk drive, a read only memory (ROM), or a random access memory (RAM).

The control unit 15 operates according to the control program to control the overall operation of the operation unit 10, the analysis unit 11, the display unit 12, the communication unit 13, and the storage unit 14. For example, in a case in which an analysis start command is input from the operation unit 10, the control unit 15 operates the analysis unit 11 according to a predetermined analysis process. Then, in a case in which the analysis result generated by the analysis unit 11 is input, the control unit 15 displays the analysis result on the display unit 12 and stores the analysis result in the storage unit 14.

An analysis process of the immunochromatographic apparatus generally includes a step of measuring a predetermined reaction time elapsed since the start of analysis, a step of capturing an image of a chromatography test piece after a predetermined reaction time elapses, and a step of digitizing the color of a reactive portion included in the acquired image of the test piece to detect or quantify an analyte in a sample liquid. The reaction time is the time for which the reactive portion comes into contact with the sample liquid. In a case in which a sample liquid containing an antigen at a predetermined concentration flows through the chromatography test piece, the predetermined reaction time is appropriately set to the time for which the reactive portion is colored at a sufficient intensity for detection. In the above-mentioned analysis process, the required analysis time from the start of analysis to the completion of analysis is typically about 20 minutes.

In addition, the control unit 15 manages the state of the analysis process on the basis of, for example, the time elapsed since the start of analysis, stores analysis progress information indicating the state of progress in the storage unit 14, and updates the analysis progress information at the right time. The analysis progress information includes information indicating whether the analysis apparatus 2A is in a standby state or is performing analysis. In a case in which the analysis apparatus 2A is performing analysis, the analysis progress information includes the remaining analysis time. The remaining analysis time is acquired, for example, by subtracting the time elapsed from a predetermined required analysis time. Then, the control unit 15 transmits the analysis progress information stored in the storage unit 14 from the communication unit 13 to the other analysis apparatuses 2B to 2E through the network 3 in response to requests from the other analysis apparatuses 2B to 2E and/or at an appropriate time interval.

In addition, the control unit 15 operates according to the control program to also function as an information collection unit 20, a search unit 21, and a display control unit 22 and performs a process including an information collection step, a search step, and a display step for managing the operation of the analysis apparatus 2A and the other analysis apparatuses 2B to 2E.

In the information collection step, the information collection unit 20 collects the analysis progress information of the analysis apparatus 2A and the other analysis apparatuses 2B to 2E and collects required movement time information of each of the analysis apparatuses 2B to 2E which is the time required for the operator to move from the installation place of the analysis apparatus 2A to the installation places of the other analysis apparatuses 2B to 2E.

The analysis progress information of the analysis apparatus 2A is acquired from the storage unit 14. The analysis progress information of the other analysis apparatuses 2B to 2E is acquired from the analysis apparatuses 2B to 2E through the network 3. In a case in which the analysis apparatuses 2B to 2E transmit the analysis progress information in response to a request, an analysis progress information request signal is transmitted from the communication unit 13 to the analysis apparatuses 2B to 2E through the network 3 under the control of the information collection unit 20. The analysis progress information of the analysis apparatuses 2B to 2E is transmitted from the analysis apparatuses 2B to 2E to the analysis apparatus 2A in response to the request signal and the information collection unit 20 acquires the received analysis progress information of the analysis apparatuses 2B to 2E. In addition, in a case in which the analysis apparatuses 2B to 2E transmit the analysis progress information to the analysis apparatus 2A at an appropriate time interval, the transmitted analysis progress information of the analysis apparatuses 2B to 2E is stored in the storage unit 14 of the analysis apparatus 2A and is updated at the right time. The information collection unit 20 acquires the analysis progress information of the analysis apparatuses 2B to 2E stored in the storage unit 14.

The required movement time information of each of the analysis apparatuses 2B to 2E indicating the required movement time which is the time required for the operator to move from the installation place of the analysis apparatus 2A to the installation places of the other analysis apparatuses 2B to 2E is stored in the storage unit 14 in advance and is acquired from the storage unit 14.

In the search step, the search unit 21 searches for an analysis apparatus that is available first among the analysis apparatus 2A and the other analysis apparatuses 2B to 2E on the basis of the analysis progress information and the required movement time information collected by the information collection unit 20. In addition, being available first means that the time until the operator moves to the installation place of the analysis apparatus and can actually use the analysis apparatus in the installation place which is the movement destination is the shortest.

Then, in the display step, the display control unit 22 performs control such that information indicating the analysis apparatus that is available first searched by the search unit 21 is displayed on the display unit 12. A search method and a display method will be described below.

The process including the information collection step, the search step, and the display step is repeatedly performed at an appropriate time interval.

The hardware structure of the control unit 15 that performs various processes as the information collection unit 20, the search unit 21, and the display control unit 22 includes a central processing unit (CPU) which is a general-purpose processor, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

Each of the processing units, such as the information collection unit 20, the search unit 21, and the display control unit 22, may be configured by one of the various processors or a combination of two or more processors of the same type or different types (for example, a combination of a plurality of FPGAs and a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by one or more of the various processors as a hardware structure. In addition, specifically, the hardware structure of the various processors is an electric circuit (circuitry) obtained by combining circuit elements such as semiconductor elements.

Next, a method for searching for the analysis apparatus that is available first will be described as an example of a search process performed by the analysis apparatus 2A.

The search unit 21 acquires the waiting time of the analysis apparatus 2A and the other analysis apparatuses 2B to 2E until new analysis can be performed on the basis of the analysis progress information. As described above, the analysis progress information includes information indicating whether the analysis apparatus is in a standby state or is performing analysis as the state of the analysis apparatus. In a case in which the analysis apparatus is performing analysis, the analysis progress information includes the remaining analysis time. In a case in which the analysis apparatus is in the standby state, the search unit 21 sets the waiting time of the analysis apparatus to 0 (zero). In addition, in a case in which the analysis apparatus is performing analysis, the search unit 21 sets the waiting time of the analysis apparatus to the remaining analysis time.

Furthermore, the search unit 21 acquires the required movement time of each of the other analysis apparatuses 2B to 2E which is the time required for the operator to move from the installation place of the analysis apparatus 2A to the installation places of the other analysis apparatuses 2B to 2E on the basis of the required movement time information. Since the installation place of the analysis apparatuses 2B and 2C is the room R1 and is the same as the installation place of the analysis apparatus 2A, the required movement time of the analysis apparatus 2B and the analysis apparatus 2C is 0 (zero). In contrast, the installation place of the analysis apparatuses 2D and 2E is the room R2 and is different from the installation place of the analysis apparatus 2A and the required movement time of the analysis apparatuses 2D and 2E is $t_{12}$. The required movement time $t_{12}$ may be, for example, the time required for the operator to actually move between the room R1 and the room R2 or may be the time estimated on the basis of the distance between the room R1 and the room R2 and the average walking speed of adults.

Then, the search unit 21 compares the waiting time and the required movement time of each of the other analysis apparatuses 2B to 2E and sets the longer of the waiting time and the required movement time of each analysis apparatus as the time required for the analysis apparatus to be available (hereinafter, referred to as an available required time). Since the required movement time of the analysis apparatuses 2B and 2C is 0 (zero), the available required time of the analysis apparatuses 2B and 2C is the waiting time. In contrast, the available required time of the analysis apparatuses 2D and 2E installed in the room R2 which is different from the installation place of the analysis apparatus 2A varies depending on the waiting time of the analysis apparatuses 2D and 2E from the relationship with the required movement time $t_{12}$ of the analysis apparatuses 2D and 2E. That is, in a case in which the waiting time is shorter than the required movement time $t_{12}$, the available required time is the required movement time $t_{12}$. In a case in which the required analysis time is equal to or shorter than the required movement time $t_{12}$, the available required time is the waiting time.

Then, the search unit 21 searches for an analysis apparatus having the shortest of the waiting time of the analysis apparatus 2A and the available required times of the other analysis apparatuses 2B to 2E as the analysis apparatus that is available first.

The above-mentioned search process is individually performed by the analysis apparatuses 2A to 2E. As described above, the required movement time is based on the installation place of the analysis apparatus that performs the search process. Therefore, in the search process of the analysis apparatus 2D, the required movement time of the analysis apparatus 2E installed in the same room R2 as the analysis apparatus 2D is 0 (zero) and the available required time of the analysis apparatus 2E is the waiting time. In contrast, the required movement time of the analysis apparatuses 2A to 2C installed in the room R1 that is different from the installation place of the analysis apparatus 2D is $t_{12}$. The available required time of the analysis apparatuses 2A to 2C is the required movement time $t_{12}$ in a case in which the waiting time is shorter than the required movement time $t_{12}$ and is the waiting time in a case in which the waiting time is equal to or longer than the required movement time $t_{12}$.

FIGS. 3 and 4 illustrate examples of the search results. FIG. 3 illustrates the search results obtained by the analysis apparatus 2A and FIG. 4 illustrates the search results obtained by the analysis apparatus 2D. In this example, it is assumed that the required movement time $t_{12}$ between the room R1 in which the analysis apparatuses 2A to 2C are installed and the room R2 in which the analysis apparatuses 2D and 2E are installed is 10 minutes.

As illustrated in FIGS. 3 and 4, the waiting time of the analysis apparatus 2A is 15 minutes, the waiting time of the analysis apparatus 2B is 5 minutes, the waiting time of the analysis apparatus 2C is 15 minutes, the waiting time of the analysis apparatus 2D is 0 (zero), and the waiting time of the analysis apparatus 2E is 10 minutes.

In a case in which the analysis apparatus that is available first is searched by only the waiting time under the above-mentioned conditions, the analysis apparatus 2D having the shortest waiting time is searched as the analysis apparatus that is available first by any of the search process of the analysis apparatus 2A and the search process of the analysis apparatus 2D. Information indicating that the analysis apparatus 2D is the analysis apparatus that is available first is displayed on the display screen of the display panel 12a of the analysis apparatus 2A. In a case in which the operator who views the display screen of the display panel 12a of the analysis apparatus 2A moves from the room R1 in which the analysis apparatus 2A is installed to the room R2 in which the analysis apparatus 2D is installed, the analysis apparatus 2B installed in the room R1 is available while the operator is moving and the opportunity to use the analysis apparatus 2B is lost. As a result, operation efficiency is reduced. In this case, for the operator who is in the room R1, the analysis apparatus 2B is the analysis apparatus that is available first. For the operator who is in the room R2, the analysis apparatus 2D is the analysis apparatus that is available first.

In contrast, in a case in which the installation places of the analysis apparatuses are considered, in the search process of the analysis apparatus 2A, the required movement time of the analysis apparatuses 2B and 2C is 0 (zero) and the required movement time of the analysis apparatuses 2D and 2E is 10 minutes. As illustrated in FIG. 3, the available required time, that is, the longer of the waiting time and the required movement time of the analysis apparatus 2B is 5 minutes, the available required time of the analysis apparatus 2C is 15 minutes, the available required time of the analysis apparatus 2D is 10 minutes, and the available required time of the analysis apparatus 2E is 10 minutes. Therefore, the analysis apparatus 2B having the shortest of the waiting time of the analysis apparatus 2A and the available required time of each of the other analysis apparatuses 2B to 2E is the analysis apparatus that is available first. Similarly, in the search process of the analysis apparatuses 2B and 2C installed in the same room R1 as the analysis apparatus 2A, the analysis apparatus 2B is the analysis apparatus that is available first.

Then, information indicating that the analysis apparatus 2B is the analysis apparatus that is available first is displayed on the display units 12 of the analysis apparatuses 2A to 2C. Therefore, the operator who views the information displayed on the display unit 12 of any of the analysis apparatuses 2A to 2C can stay in the room R1 in which the analysis apparatus 2B is installed and can use the analysis apparatus 2B.

In addition, in the search process of the analysis apparatus 2D, the required movement time of the analysis apparatuses 2A to 2C is 10 minutes and the required movement time of the analysis apparatus 2E is 0 (zero). Therefore, as illustrated in FIG. 4, the available required time of the analysis apparatus 2A is 15 minutes, the available required time of the analysis apparatus 2B is 10 minutes, the available required time of the analysis apparatus 2C is 15 minutes, and the available required time of the analysis apparatus 2E is 10 minutes. Therefore, the analysis apparatus 2D having the shortest of the waiting time of the analysis apparatus 2D and the available required time of each of the other analysis apparatuses 2A to 2C and 2E is the analysis apparatus that is available first. Similarly, in the search process of the analysis apparatus 2E installed in the same room R2 as the analysis apparatus 2D, the analysis apparatus 2D is the analysis apparatus that is available first.

Then, information indicating that the analysis apparatus 2D is the analysis apparatus that is available first is displayed on the display units 12 of the analysis apparatuses 2D to 2E. Therefore, the operator who views the information displayed on the display unit 12 of any of the analysis apparatuses 2D and 2E can stay in the room R2 in which the analysis apparatus 2D is installed and can use the analysis apparatus 2D.

As such, since the installation places of the analysis apparatuses 2A to 2E are considered in the search processes of the analysis apparatuses 2A to 2E, the analysis apparatus that is available first is appropriately searched. Therefore, it is possible to improve the operation efficiency of the analysis apparatuses 2A to 2E and to improve the usability of the analysis system 1.

In the above description, the required movement time information of each of the other analysis apparatuses indicating the required movement time which is the time required for the operator to move from the installation place of the analysis apparatus that performs a search process to the installation places of the other analysis apparatuses is stored in advance in the storage unit 14 of the analysis apparatus that performs the search process. However, the required movement time information may be acquired on the basis of the installation places of the other analysis apparatuses.

Specifically, the required movement time $t_{12}$ between the room R1 in which the analysis apparatuses 2A to 2C are installed and the room R2 in which the analysis apparatuses 2D and 2E are installed is stored in the storage units 14 of the analysis apparatuses 2A to 2E so as to be associated with the installation places.

For example, in the search process of the analysis apparatus 2A, the analysis apparatus 2A (information collection unit 20) acquires the installation places of the other analysis apparatuses 2B to 2E from the analysis apparatuses 2B to 2E through the network 3. Then, the analysis apparatus 2A sets the required movement time of the analysis apparatuses 2B and 2C installed in the same room R1 as the analysis apparatus 2A to 0 (zero) and sets the required movement time of the analysis apparatuses 2D and 2E installed in the room R2 which is different from the installation place of the analysis apparatus 2A to the required movement time $t_{12}$ stored in the storage unit 14 so as to be associated with the rooms R1 and R2, on the basis of the acquired installation places of the other analysis apparatuses 2B to 2E.

Similarly, in the search process of the analysis apparatus 2D, the analysis apparatus 2D acquires the installation places of the other analysis apparatuses 2A to 2C and 2E from the analysis apparatuses 2A to 2C and 2E through the network 3. Then, the analysis apparatus 2D sets the required movement time of the analysis apparatus 2E installed in the same room R2 as the analysis apparatus 2D to 0 (zero) and sets the required movement time of the analysis apparatuses 2A to 2C installed in the room R1 which is different from the installation place of the analysis apparatus 2D to the required movement time $t_{12}$ stored in the storage unit 14 so as to be associated with the rooms R1 and R2, on the basis of the acquired installation places of the other analysis apparatuses 2A to 2C and 2E.

Next, a method for displaying information indicating the analysis apparatus that is available first will be described, using the display of the analysis apparatus 2A based on the search results of the analysis apparatus 2A illustrated in FIG. 3 as an example.

In an example illustrated in FIG. 5, a list of the identifiers (identifications (IDs)), state, waiting time, and required movement time of each of the analysis apparatuses 2A to 2E connected to the network 3 is displayed on the display screen of the display panel 12a under the control of the display control unit 22. In addition, the required movement time is based on the room R1 in which the analysis apparatus 2A is installed. The, a mark M indicating that the analysis apparatus 2B is the analysis apparatus that is available first is also displayed in the field of the analysis apparatus 2B which is the analysis apparatus that is available first.

Further, instead of the display of the mark M, the fields of the analysis apparatuses 2A to 2E may be arranged in ascending order of the available required time and the field of the analysis apparatus 2B may be displayed at the top. In this case, it is possible to indicate that the analysis apparatus 2B is the analysis apparatus that is available first.

In an example illustrated in FIG. 6, the identifier and state of the analysis apparatus 2B which is the analysis apparatus that is available first are displayed on the display screen of the display panel 12a under the control of the display control unit 22. In a case in which the analysis apparatus 2B is performing analysis, the time required for analysis is also displayed on the display screen. As such, in a case in which only the information of the analysis apparatus that is available first is displayed, the size of the display screen can be less than that in a case in which a list of the information of all of the analysis apparatuses 2A to 2E is displayed. Therefore, it is possible to reduce the size of the analysis apparatus.

In addition, a method for displaying information indicating the analysis apparatus that is available first is not limited to the above-mentioned example. For example, the display aspect of the display unit 12 may be different in a case in which the analysis apparatus that is available first is the host analysis apparatus and in a case in which the analysis apparatus that is available first is another analysis apparatus. In addition, the display aspect of the display unit 12 may be different in a case in which the analysis apparatus that is available first is another analysis apparatus which is in the same installation place as the host analysis apparatus and in a case in which the analysis apparatus that is available first is another analysis apparatus in an installation place different from the installation place of the host analysis apparatus.

For example, in the search process of the analysis apparatus 2A, in a case in which the analysis apparatus 2A is the analysis apparatus that is available first, the color of a backlight of the display screen of the display panel 12a in the analysis apparatus 2A is blue. In a case in which the analysis apparatus 2B or the analysis apparatus 2C installed in the same room R1 as the analysis apparatus 2A is the analysis apparatus that is available first, the color of the backlight of the display screen of the display panel 12a in the analysis apparatus 2A is yellow. In a case in which the analysis apparatus 2D or the analysis apparatus 2E installed in the room R2 different from the installation place of the analysis apparatus 2A is the analysis apparatus that is available first, the color of the backlight of the display screen of the display panel 12a in the analysis apparatus 2A is red.

As such, since the display aspect is different, the operator can visually recognize the location of the analysis apparatus that is available first easily and quickly. In addition, the different display aspect is not limited to the color of the backlight of the display screen of the display panel 12a and may be the lighting state (turn-on, blinking, or turn-off) of the backlight or a combination of the color and the lighting state. In a case in which the display unit 12 further includes a display lamp such as a light emitting diode (LED), the different display aspect may be the color and/or lighting state (turn-on, blinking, or turn-off) of the display lamp or a combination of the color of the backlight of the display screen of the display panel 12a and the color and/or lighting state of the display lamp.

In the above-described embodiment, the control units 15 of the analysis apparatuses 2A to 2E have the same functions (the information collection unit 20, the search unit 21, and the display control unit 22). However, at least one analysis apparatus that presents information indicating the analysis apparatus that is available first to the operator may be in each installation place. For example, assuming that the analysis apparatus 2A presents the information in the room R1 and the analysis apparatus 2D presents the information in the room R2, the functions of the information collection unit 20, the search unit 21, and the display control unit 22 may be removed from the control units 15 of the analysis apparatuses 2B, 2C and 2E.

A program may be provided which causes a processor to perform each step (the information collection step, the search step, and the display step) performed by the control unit 15. The program can be recorded on a non-transitory recording medium from which the processor can read a program and then provided. Examples of the "processor readable recording medium" include an optical medium, such as a compact disc-ROM (CD-ROM), and a magnetic recording medium, such as a memory card. In addition, the program may be downloaded through the network and then provided.

As described above, the specification discloses an analysis apparatus that is connected to other analysis apparatuses so as to be communicable therewith and comprises: an information collection unit that collects analysis progress information of the host analysis apparatus and the other analysis apparatuses and required movement time information of each of the other analysis apparatuses indicating the required movement time which is the time required for an operator to move from an installation place of the host analysis apparatus to installation places of the other analysis apparatuses; a search unit that searches for an analysis apparatus that is available first among the host analysis apparatus and the other analysis apparatuses on the basis of the analysis progress information and the required movement time information collected by the information collection unit; and a display control unit that displays information indicating the analysis apparatus that is available first searched by the search unit on a display unit of the analysis apparatus.

The search unit acquires the waiting times of the host analysis apparatus and the other analysis apparatuses until new analysis can be performed, on the basis of the analysis progress information, and searches for the analysis apparatus that is available first, on the basis of the waiting time of the host analysis apparatus and the longest of the waiting times and the required movement times of the other analysis apparatuses.

The display control unit performs control such that a display aspect of the display unit is different in a case in which the analysis apparatus that is available first searched by the search unit is the host analysis apparatus and in a case in which the analysis apparatus that is available first searched by the search unit is another analysis apparatus.

The display control unit performs control such that the display aspect of the display unit is different in a case in which the analysis apparatus that is available first searched by the search unit is another analysis apparatus which is in the same installation place as the host analysis apparatus and in a case in which the analysis apparatus that is available first searched by the search unit is another analysis apparatus which is in an installation place different from the installation place of the host analysis apparatus.

An analysis system disclosed in the specification comprises a plurality of analysis apparatuses that are dispersively installed in a plurality of installation places and are connected so as to communicable with each other. At least one analysis apparatus in each installation place is the analysis apparatus.

The specification discloses a method for managing a plurality of analysis apparatuses that are connected so as to be communicable with each other. The management method comprises: an information collection step of allowing a processor of at least one analysis apparatus to collect analysis progress information of the host analysis apparatus and the other analysis apparatuses and required movement time information of each of the other analysis apparatuses indicating a required movement time which is a time required for an operator to move from an installation place of the host analysis apparatus to installation places of the other analysis apparatuses; a search step of allowing the processor to search for an analysis apparatus that is available first among the host analysis apparatus and the other analysis apparatuses on the basis of the analysis progress information and the required movement time information collected in the information collection step; and a display step of allowing the processor to display information indicating the analysis apparatus that is available first searched in the search step on a display unit of the analysis apparatus.

In the search step, the processor acquires waiting times of the host analysis apparatus and the other analysis apparatuses until new analysis can be performed, on the basis of the analysis progress information, and searches for the analysis apparatus that is available first, on the basis of the waiting time of the host analysis apparatus and the longest of the waiting times and the required movement times of the other analysis apparatuses.

In the display step, the processor performs control such that a display aspect of the display unit is different in a case in which the analysis apparatus that is available first searched in the search step is the host analysis apparatus and in a case in which the analysis apparatus that is available first searched in the search step is another analysis apparatus.

In the display step, the processor performs control such that the display aspect of the display unit is different in a case in which the analysis apparatus that is available first searched in the search step is another analysis apparatus which is in the same installation place as the host analysis apparatus and in a case in which the analysis apparatus that is available first searched in the search step is another analysis apparatus which is in an installation place different from the installation place of the host analysis apparatus.

In addition, the specification discloses a program that causes a processor to perform each step of the management method.

The invention can improve the operation efficiency and usability of a plurality of analysis apparatuses that can perform the same type of analysis.

The embodiment of the invention has been described above in detail. However, the embodiment is just an example and various modifications and changes in the invention can be made without departing from the scope and spirit of the invention. This application is based on Japanese Patent Application (JP2017-014590) filed on Jan. 30, 2017, the content of which is incorporated herein by reference in its entirety.

EXPLANATION OF REFERENCES

1: analysis system
2A to 2E: analysis apparatus
3: network
10: operation unit
11: analysis unit
12: display unit
12a: display panel
13: communication unit
14: storage unit
15: control unit
20: information collection unit
21: search unit
22: display control unit
M: mark
R1: room (installation place)
R2: room (installation place)

What is claimed is:

1. An analysis system comprising:
a plurality of analysis apparatuses that are dispersively installed in a plurality of installation places and are connected so as to be communicable with ach other, wherein at least one analysis apparatus in each installation place is a host analysis apparatus comprising:
a communication I/O interface that connects the host analysis apparatus to other analysis apparatuses;
a display; and
a processor, configured to:
collect analysis progress information of the host analysis apparatus and the other analysis apparatuses and required movement time information of each of the other analysis apparatuses indicating a required movement time which is a time required for an operator to move from an installation place of the host analysis apparatus to installation places of the other analysis apparatuses;
search for an analysis apparatus that is available first among the host analysis apparatus and the other analysis apparatuses on the basis of the analysis progress information and the required movement time information; and
display information indicating the searched analysis apparatus that is available first on the display.

2. The analysis system according to claim 1, wherein the processor is configured to acquire waiting times of the host analysis apparatus and the other analysis apparatuses until new analysis can be performed, on the basis of the analysis progress information, and search for the analysis apparatus that is available first, on the basis of the waiting time of the host analysis apparatus and longest of the waiting times and the required movement times of the other analysis apparatuses.

3. The analysis system according to claim 1, wherein the processor is configured to perform control such that a display manner of the display is different in a case in which the searched analysis apparatus that is available first is the host analysis apparatus and in a case in which the searched analysis apparatus that is available first is another analysis apparatus.

4. The analysis system according to claim 2, wherein the processor is configured to perform control such that a display manner of the display is different in a case in which the searched analysis apparatus that is available first is the host analysis apparatus and in a case in which the searched anal sis apparatus that is available first is another analysis apparatus.

5. The analysis system according to claim 3, wherein the processor is configured to perform control such that the display manner of the display is different in a case in which the searched analysis apparatus that is available first is another analysis apparatus which is in the same installation place as the host analysis apparatus and in a case in which the searched analysis apparatus that is available first is another analysis apparatus which is in an installation place different from the installation place of the host analysis apparatus.

6. The analysis system according to claim 4, wherein the processor is configured to perform control such that the display manner of the display is different in a case in which the searched analysis apparatus that is available first is another analysis apparatus which is in the same installation place as the host analysis apparatus and in a case in which the searched analysis apparatus that is available first is another analysis apparatus which is in an installation place different from the installation place of the host analysis apparatus.

7. A method for managing a plurality of analysis apparatuses that are connected to each other so as to be communicable with each other, at least one of the plurality of analysis apparatuses being a host analysis apparatus, the method comprising:

an information collection step, executed by a processor of the host analysis apparatus, to collect analysis progress information of the host analysis apparatus and the other analysis apparatuses and required movement time information of each of the other analysis apparatuses indicating a required movement time which is a time required for an operator to move from an installation place of the host analysis apparatus to installation places of the other analysis apparatuses;

a search step, executed by the processor, to search for an analysis apparatus that is available first among the host analysis apparatus and the other analysis apparatuses on the basis of the analysis progress information and the required movement time information collected in the information collection step; and a display step, executed by the processor, to display information indicating the analysis apparatus that is available first searched in the search step on a display of the host analysis apparatus.

8. The management method according to claim 7, wherein, in the search step, the processor acquires waiting times of the host analysis apparatus and the other analysis apparatuses until new analysis can be performed, on the basis of the analysis progress information, and searches for the analysis apparatus that is available first, on the basis of the waiting time of the host analysis apparatus and longest of the waiting times and the required movement times of the other analysis apparatuses.

9. The management method according to claim 7, wherein, in the display step, the processor performs control such that a display manner of the display is different in a case in which the analysis apparatus that is available first searched in the search step is the host analysis apparatus and in a case in which the analysis apparatus that is available first searched in the search step is another analysis apparatus.

10. The management method according to claim 8, wherein, in the display step, the processor performs control such that a display manner of the display is different in a case in which the analysis apparatus that is available first searched in the search step is the host analysis apparatus and in a case in which the analysis apparatus that is available first searched in the search step is another analysis apparatus.

11. The management method according to claim 9, wherein, in the display step, the processor performs control such that the display manner of the display is different in a case in which the analysis apparatus that is available first searched in the search step is another analysis apparatus which is in the same installation place as the host analysis apparatus and in a case in which the analysis apparatus that is available first searched in the search step is another analysis apparatus which is in an installation place different from the installation place of the host analysis apparatus.

12. The management method according to claim 10, wherein, in the display step, the processor performs control such that the display manner of the display is different in a case in which the analysis apparatus that is available first searched in the search step is another analysis apparatus which is in the same installation place as the host analysis apparatus and in a case in which the analysis apparatus that is available first searched in the search step is another analysis apparatus which is in an installation place different from the installation place of the host analysis apparatus.

13. A non-transitory computer readable medium storing a program that causes a processor of a host analysis apparatus to:

collect analysis progress information of the host analysis apparatus and other analysis apparatuses and required movement time information of each of the other analysis apparatuses indicating a required movement time which is a time required for an operator to move from an installation place of the host analysis apparatus to installation places of the other analysis apparatuses;

search for an analysis apparatus that is available first among the host analysis apparatus and the other analysis apparatuses on the basis of the analysis progress information and the required movement time information; and display information indicating the analysis apparatus that is available first on a display of the host analysis apparatus.

* * * * *